(12) United States Patent
Moser et al.

(10) Patent No.: US 6,664,228 B1
(45) Date of Patent: Dec. 16, 2003

(54) PHOTOSELECTIVE MARKING OF BIOLOGICAL TARGETS

(75) Inventors: Jörg G Moser, Düsseldorf (DE); Wolfgang Neuberger, Labaun (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 391 days.

(21) Appl. No.: 09/636,819

(22) Filed: Aug. 10, 2000

(51) Int. Cl.$^7$ .................. A61K 38/00; A61K 39/00; C07K 16/00
(52) U.S. Cl. ................ 514/8; 514/2; 514/12; 514/16; 530/387.1; 435/460; 424/198.1
(58) Field of Search ............ 514/2, 8, 12, 16; 530/387.1; 435/460; 424/198.1

(56) References Cited

U.S. PATENT DOCUMENTS

| | | |
|---|---|---|
| 4,086,254 A | 4/1978 | Wierenga |
| 4,590,211 A | 5/1986 | Voorhees et al. |
| 4,671,958 A | 6/1987 | Rodwell et al. |

OTHER PUBLICATIONS

Ruebner et al. 1999. Proceedings of the National Academy of Sciences, Dec., vol. 96, No. 26, pp. 14692–14693.*

* cited by examiner

Primary Examiner—Brenda Brumback
Assistant Examiner—Billy D. Chism
(74) Attorney, Agent, or Firm—BJ Associates; Bolesh J. Skutnik

(57) ABSTRACT

A drug delivery system and methods are provided wherein a therapeutic/diagnostic agent or a component of the immune system is directed to particular cells in a selected organ or a specific site. Such a system can be formed by a photoselective compound generally described as V-M-P-C. V is a vector component suitable to target particular cells in a selected organ or site, where the type of the cell or antigen does not have to be specific to the desired treatment site. M is a marker component that is capable of being targeted by a therapeutic/diagnostic agent or a component of the immune system. P is a photocleavable or photosensitive bond, and C is a cap component rendering M ineffective. C is connected to M by the photocleavable or photosensitive bond. The photoselective compound is administered and marks targets of a certain kind of cell or a specific site. Then radiation of a specific wavelength or wavelength range is applied to the geometric volume that is to be treated, uncapping the M sites in the desired treatment volume. Therapeutic or diagnostic agents can be subsequently or concurrently administered in a form that specifically targets the uncapped sites of M. The therapeutic or diagnostic agent can be a drug, a radioactive compound, a fluorescent compound or a photosensitiser. Additional components, such as multiplier molecules, can also be inserted into the basic V-M-P-C scheme. Moreover, the marker component can be such that after the removal of the cap component, components of the immune system can bind to M and thus concentrate at a desired site. The present invention facilitates the delivery of therapeutic/diagnostic agents or components of the immune system to particular cells in a selected organ or a specific site, and therefore, minimizes the potential harmful effect of the agents to the normal cells in the rest of the body.

8 Claims, 3 Drawing Sheets

200

PHOTOSELECTIVE MARKING OF BIOLOGICAL TARGETS

BACKGROUND OF THE INVENTION

1. Field of the Invention

The invention relates to phototherapy, wherein a drug delivery system is used to target cells of a specific kind in a selected organ or part of the body, even when the cells are not specific or sufficiently specific to the location.

2. Invention Disclosure Statement

Drug therapies need to be increasingly selective to avoid side effects. It is beneficial for drugs that are administered systemically to target only specific cells in selective locations, and thus avoid harmful effects on normal cells in the rest of the body.

To achieve this goal, different methods have been attempted. Vectors, such as lectins, selecting, antibodies have been developed and coupled to therapeutic agents to accomplish this selectivity. For example, U.S. Pat. No. 4,671,958(J. Rodwell and T. McKearn) described a method for delivering of compounds to target sites by conjugating the compounds to antibodies. When such compound-antibody complexes are administered to a patient, the antibody binds to desired target antigen, such as certain tumor cells, in vivo. This antigen-antibody reaction will trigger the patient's serum complement system, and attached compounds will be cleaved off by the proteolytic enzymes of the complement system and become active. However, since an antibody will bind to its counterpart antigen existing anywhere in the body, this method fails to achieve the desired selectivity when the antigenic cells are not particularly specific to a selected organ or part of a body.

Another attempt has been made using photoactivation. In this method, a drug is activated by radiation in the desired local area. For example, U.S. Pat. No. 4,590,211(J. Voorhees et al) describes a method comprising the administration of a pro-drug to a patient. A pro-drug is formed by a therapeutic compound chemically combined with another moiety by a photocleavable bond and the combination is inactive. Subsequent ultraviolet radiation of the diseased area will cleave the photocleavable bond and release the therapeutic compound. U.S. Pat. No. 4,086,254 (W. Wierenga) describes new compounds that have a photocleavable group removable by irradiation. The compounds have reduced activity in the uncleaved state and provide a therapeutically active compound upon irradiation at the desired site. However, the photoactivation method used in these patents has certain limits. The drug, which is delivered in this way, does not bind to any specific cells or particular antigens. Therefore, they do not achieve the cell-specific effect in a particular organ. Generally, such systems are used only to treat the inflammatory and/or proliferative skin diseases.

The present invention provides a system that delivers compounds to specific cells in selected organs or part of a body by using photoselective markers.

BRIEF SUMMARY OF THE INVENTION

It is an object of the present invention to provide a system that delivers therapeutic compounds to particular cells in selected organs, thereby preventing potential harmful side effects of such compounds on the normal cells in the rest of the body.

It is another object of the present invention to use a vector component that will target a specific site or particular cells such that the connected therapeutic compounds will be delivered to the site or cells.

Still another object of the present invention is to use a marker component complexed to the vector component, and still capable of being targeted by therapeutic/diagnostic agents or components of the immune system.

Yet another object of the present invention is to use a cap component connected to the marker component by a photocleavable bond or a photosensitive bond, so that radiation in a desirable site cleaves the cap component off and render the marker component available for binding to a therapeutic or diagnostic agent or a component of the immune system.

It is a further object of the present invention to direct therapeutic/diagnostic agents or components of the immune system only at a desired site or organ through the specific interaction of the marker component and the therapeutic or diagnostic agents/components.

Briefly stated, the present invention provides a drug delivery system wherein a therapeutic/diagnostic agent or a component of the immune system is directed to particular cells in a selected organ or a specific site. Such a system can be formed by a photoselective compound generally described as V-M-P-C. V is a vector component suitable to target particular cells in a selected organ or site, where the type of the cell or antigen does not have to be specific to the desired treatment site. M is a marker component that is capable of being targeted by a therapeutic/diagnostic agent or a component of the immune system. P is a photocleavable or photosensitive bond, and C is a cap component rendering M ineffective. C is connected to M by the photocleavable or photosensitive bond. The photoselective compound is administered and marks targets of a certain kind of cell or a specific site. Then radiation of a specific wavelength or wavelength range is applied to the geometric volume that is to be treated, uncapping the M sites in the desired treatment volume. Therapeutic or diagnostic agents can be subsequently or concurrently administered in a form that specifically targets the uncapped sites of M. The therapeutic or diagnostic agent can be a drug, a radioactive compound, a fluorescent compound or a photosensitiser. Additional components, such as multiplier molecules, can also be inserted into the basic V-M-P-C scheme. Moreover, the marker component can be such that after the removal of the cap component, components of the immune system can bind to M and thus concentrate at a desired site. The present invention facilitates the delivery of therapeutic/diagnostic agents or components of the immune system to particular cells in a selected organ or a specific site, and therefore, minimizes the potential harmful effect of the agents to the normal cells in the rest of the body.

The above, and other objects, features and advantages of the present invention will become apparent from the following description read in conjunction with the accompanying drawings.

DETAILED DESCRIPTION OF PREFERRED EMBODIMENTS

The present invention describes a delivery system (a photoselective compound) that can direct either a therapeutic/diagnostic agent or a component of the immune system to particular cells or antigens at a desired site. The cell/antigen-specific targeting is achieved by using a vector component that has a selective binding nature, while the site-specific targeting is achieved by exploiting a photocleavable or photosensitive bond. Radiation is applied only to the treatment site to break the photocleavable/ photosensitive bond, which causes the photoselective compound to be activated, and in turn the activated compound guides therapeutic/diagnostic agents or components of the immune system to only a desired site. Such a delivery system is desirable for several reasons. First, it makes the treatment more effective and efficient because therapeutic or diagnostic agents are concentrated at desired sites and cells. Second, it minimizes the harmful effect of the therapeutic or diagnostic agents because normal cells in the rest of the body are not affected. Moreover, this delivery system provides a non-invasive way for practitioners to deliver agents in both a cell/antigen-specific and location-specific manner.

Figure 1:
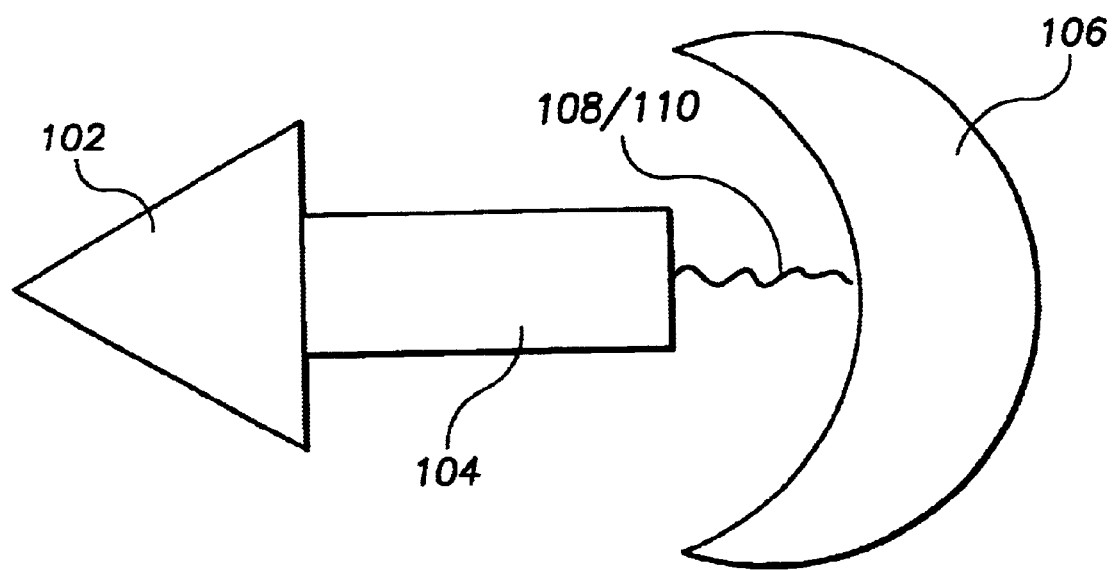
FIG. 1 shows the construction of a photoselective compound.

FIG. 1 shows the structure of photoselective compound 100. Compound 100 is constructed by combining vector component 102, marker component 104, and cap component 106 together. Vector component 102 can be selected from lectins, selecting, antibodies or any other molecules that can target specifically to particular cells or antigens, where the cell type does not have to be unique to the desired location. Marker component 104 is a molecular fragment that can be targeted by therapeutic/diagnostic agents or components of the immune system when it is not attached to cap component 106. Cap component 106 is any molecular structures that are capable of rendering marker component 102's binding ability to other molecules (except the already bound vector component 102) ineffective while cap component 106 is bound to marker component 104. Cap component 106 is connected to marker component 104 by photocleavable bond 108 or photosensitive bond 110 (in which the bond can, for example, be cleaved by highly reactive forms of oxygen produced by activating a photosensitizer in the vicinity of compound 100).

Figure 2:
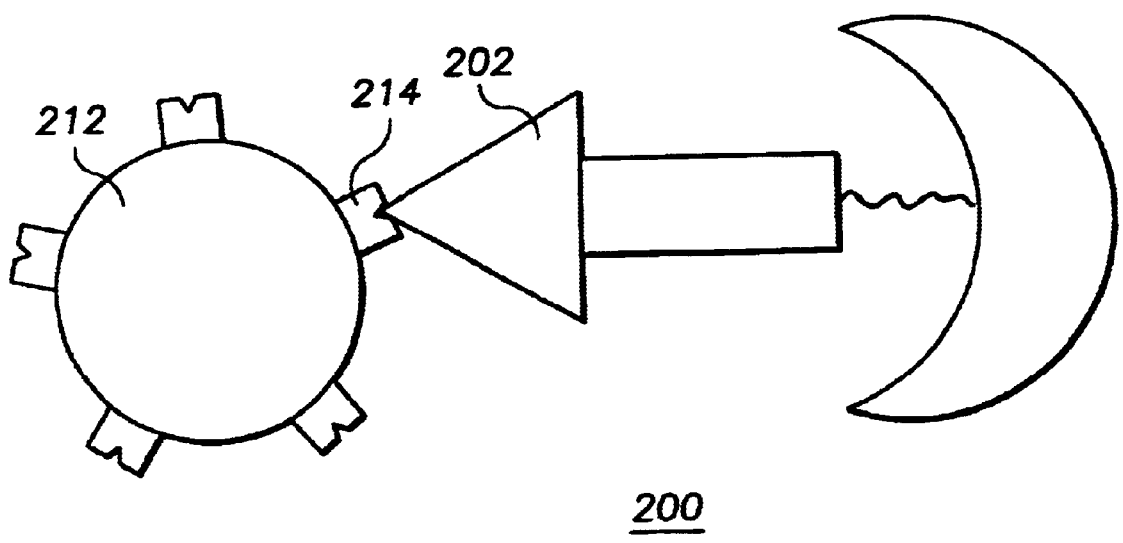
FIG. 2 shows how a photoselective compound marks desired cells or antigens.

FIG. 2 illustrates how the photoselective compound 200 marks desired cells 212 by attaching to antigens 214 of cell 212. After compound 200 is administered systemically, it binds to a particular cell type or a specific antigen because of the selective nature of vector component 202. Cell type or antigen 214 does not have to be unique to the desired organ or location.

Figure 3A:
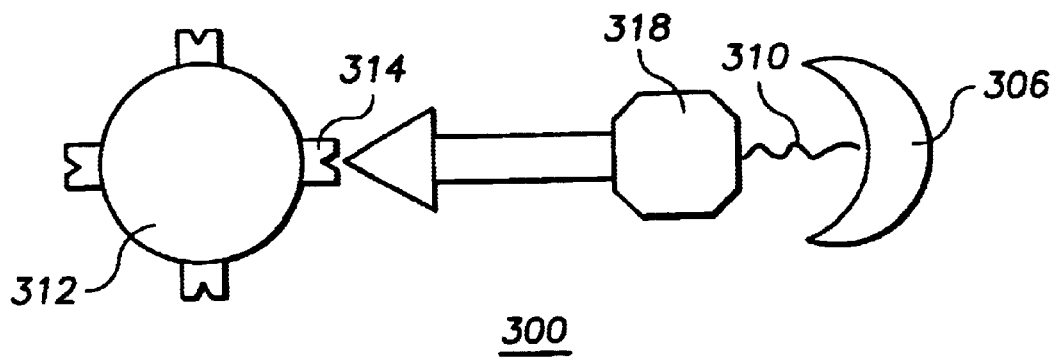
FIG. 3 demonstrates preferred embodiments of the present invention.
Figure 3B:
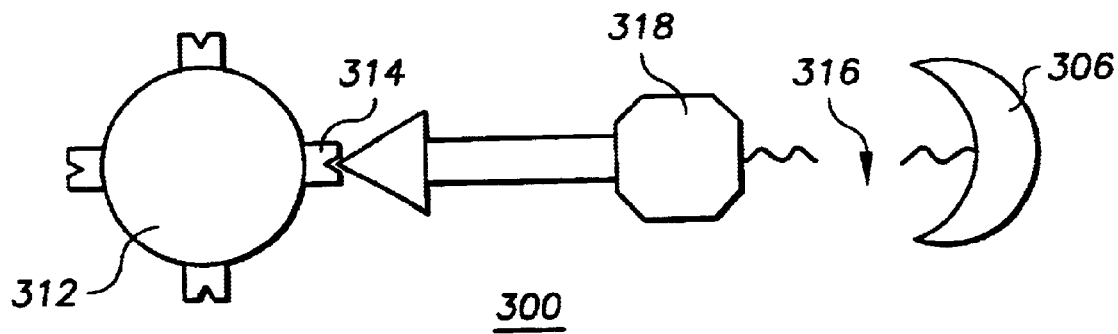

FIG. 3 demonstrates preferred embodiments of the present invention. 318 can be either a pharmaceutical active compound, a target for the immune system, a photosensitiser, or a biotin. In the case where 318 is biotin, the counterpart avidin is attached to a pharmaceutical active compound or a photosensitixer. FIG. 3a shows compounds 300 marking particular cell 312 by attaching to antigen 314 on cell 312. FIG. 3b shows the removal of cap component 306. Radiation 316 is applied to a specified organ or location, causing the breaking of photocleavable or photosensitive bond 310, and in turn causing the removal of cap component 306.

The present invention is further illustrated by the following examples, but is not limited thereby.

Example 1

One example of a possible marker component of the photoselective compound is a Biotin-Avidin formulation. It is well known that Biotin can be conjugated to proteins such as antibodies, lectins, and nucleic acids which are capable of functioning as a vector component in the present invention. Avidin can be conjugated to enzymes or other proteins with minimal loss of activity. There is also a high affinity between Biotin and Avidin. A Biotin-Avidin complex can, therefore, function as a marker component in the present invention, and links the vector (at the Biotin end) and the potential. therapeutic or diagnostic agents (at the Avidin end).

Example 2

One example of a possible cap component is a Cyclodextrin or Cyclodextrin oligomer structure linked to the marker component through a photosensitive bond. The synthesis of such structures is well known. They can function as a carrier of a photosensitizer such as Phthalocyanine. The Cyclodextrin can be cleaved by light, and thus activate the photosensitizer and release the highly reactive form of oxygen, which in turn will break the photosensitive bond and remove the Cyclodextrin cap. As a result, the uncapped marker site of the photoselective compound is ready for the binding of either a therapeutic/diagnostic agent or a component of the body's immune system.

Having described preferred embodiments of the invention with reference to the accompanying drawings, it is to be understood that the invention is not limited to the precise embodiments' and that various changes and modifications may be effected therein by skilled in the art without departing from the scope or spirit of the invention as defined in the appended claims.

What is claimed is:

1. A compound, which functions to direct a therapeutic/ diagnostic agent or a component of an immune system to a desired site, comprising:
    a vector component, wherein said vector component is a molecule for specifically targeting particular cells or antigens;
    marker component bonded to said vector component, wherein said marker component binds to a therapeutic/ diagnostic agent, a photosensitizer, or a component of an immune system;
    a cap component, bonded to said marker component, wherein said cap component is a molecular structure that renders said marker component unable to bind to a therapeutic/diagnostic agent, a photosensitizer or a component of an immune system until said cap component is removed; and
    a photocleavable/photosensitive bond, which attaches said cap component to said marker component.

2. The compound according to claim 1, wherein said vector component is selected from the group consisting of lectins, selecting, antibodies, nucleic acids, and hormones.

3. The compound according to claim 1, wherein said marker component is a Biotin-Avidin complex.

4. The compound according to claim 1, wherein said cap component is selected from the group consisting of Cyclodextrin and Cyclodextrin oligomers.

5. A therapeutic/diagnostic procedure comprising the steps of:
    a. administering the compound of claim 1, wherein said photoselective compound comprises a vector component, a marker component, a cap component, and wherein said cap component is attached to said marker component by a photocleavable/photoselective bond;
    b. irradiating preselected treatment sites with radiation of specified wavelength or wavelength range to cleave said photocleavable/photosensitive bond and, in turn, cause the removal of said cap component; and c. subsequently or concurrently administering a therapeutic/diagnostic agent capable of targeting said marker component, wherein binding of said agent and said marker component restricts said agent at the preselected treatment sites.

6. A therapeutic/diagnostic procedure comprising the steps of:

a. administering the compound of claim 1, wherein said photoselective compound comprises a vector component, a marker component, a cap component, wherein said cap component is bonded to said marker component by a photocleavable/photoselective bond, wherein said marker component can be recognized by components of a body's immune system when said marker component is not bonded to said cap component;

b. irradiating preselected treatment sites with radiation of specified wavelength or wavelength range to cleave said photocleavable/photosensitive bond and in turn cause removal of said cap component, revealing said marker component and resulting in interactions between components of the immune system and said marker component.

7. The procedure as claimed in claim 5, wherein said radiation can be accomplished by exposing the compound to natural sunlight or spectral parts therefrom.

8. The procedure as claimed in claim 6, wherein said radiation can be accomplished by exposing the compound to natural sunlight or spectral parts therefrom.

* * * * *